(12) United States Patent
Changaris et al.

(10) Patent No.: US 12,171,737 B2
(45) Date of Patent: Dec. 24, 2024

(54) METHODS FOR REDUCING THE SYMPTOMS OF NEURODEGENERATIVE DISEASE IN A HUMAN

(71) Applicants: David G. Changaris, Louisville, KY (US); Raymond Walker, Louisville, KY (US)

(72) Inventors: David G. Changaris, Louisville, KY (US); Raymond Walker, Louisville, KY (US)

( * ) Notice: Subject to any disclaimer, the term of this patent is extended or adjusted under 35 U.S.C. 154(b) by 0 days.

(21) Appl. No.: 17/953,749

(22) Filed: Sep. 27, 2022

(65) Prior Publication Data
US 2023/0130195 A1 Apr. 27, 2023

Related U.S. Application Data

(60) Provisional application No. 63/249,152, filed on Sep. 28, 2021.

(51) Int. Cl.
*A61K 31/201* (2006.01)
*A61K 9/00* (2006.01)
(Continued)

(52) U.S. Cl.
CPC .......... *A61K 31/201* (2013.01); *A61K 9/0014* (2013.01); *A61K 9/06* (2013.01);
(Continued)

(58) Field of Classification Search
CPC .... A61K 31/201; A61K 47/44; A61K 9/0014; A61K 9/06; A61K 9/4858; A61K 31/20; A61K 31/202; A61K 31/23; A61P 25/28
See application file for complete search history.

(56) References Cited

U.S. PATENT DOCUMENTS

| 2,763,936 A | * | 9/1956 | Newman | A61B 5/22 33/512 |
| 2006/0147566 A1 | * | 7/2006 | Rull Prous | A61K 31/232 424/490 |

FOREIGN PATENT DOCUMENTS

| WO | WO-2012026662 A1 | * | 3/2012 | ........... A61K 31/201 |
| WO | WO-2018085440 A1 | * | 5/2018 | |

OTHER PUBLICATIONS

Lou et al., Cannabinoids for the treatment of refractory neuropathic pruritus in amyotrophic lateral sclerosis: A case report, Palliative Med., 36, pp. 208-211 (Year: 2022).*
(Continued)

*Primary Examiner* — Jeffrey S Lundgren
*Assistant Examiner* — Alexander K. Showalter
(74) *Attorney, Agent, or Firm* — Witters & Associates; Steve Witters

(57) ABSTRACT

A method of reducing symptoms of neurodegenerative disease in a human is provided. The method comprises applying to the human a solution or salve to at least one of the skin, the mouth, the nasal cavities, the lungs, the eyes, or the vagina of the human. The applied solution or salve comprises an effective amount of an isomerized or conjugated linoleic acid cation salt having a conjugated diene for at least a measurable improvement in the movement or mental acuity of the human and a structure of —C=C—C=C—. The measurable improvement in the movement or mental acuity of the human is within 4-6 weeks of the applying of the solution or salve. A method of making the conjugated diene and a device for measuring the reduction of systems is also provided.

14 Claims, 5 Drawing Sheets

(51) Int. Cl.
      *A61K 9/06*      (2006.01)
      *A61K 9/48*      (2006.01)
      *A61K 31/20*     (2006.01)
      *A61K 31/202*    (2006.01)
      *A61K 31/23*     (2006.01)
      *A61K 47/44*     (2017.01)
      *A61P 25/28*     (2006.01)

(52) U.S. Cl.
      CPC ............ *A61K 9/4858* (2013.01); *A61K 31/20* (2013.01); *A61K 31/202* (2013.01); *A61K 31/23* (2013.01); *A61K 47/44* (2013.01); *A61P 25/28* (2018.01)

(56) References Cited

OTHER PUBLICATIONS

Paulkuhne et al., Trends in Active Pharmaceutical Ingredient Salt Selection based on Analysis of the Orange Book Database, J. Med. Chem., 50, pp. 6665-6672 (Year: 2007).*
Garza-Rodriguez et al., Pronation and supination analysis based on biomechanical signals from Parkinson's disease patients, Artificial Intellig. Med., 84, pp. 7-22 (Year: 2018).*
Zhang et al., Green Synthesis of Conjugated Linoleic Acids from Plant Oils Using a Novel Synergistic Catalytic System, J. Agric. Food Chem.; 65, pp. 5322-5329 (Year: 2017).*
Kwon Machine Translation (Year: 2012).*

* cited by examiner

METHODS FOR REDUCING THE SYMPTOMS OF NEURODEGENERATIVE DISEASE IN A HUMAN

CROSS REFERENCE TO RELATED APPLICATIONS

This application claims priority to U.S. provisional application No. 63/249,152, filed Sep. 28, 2021, the disclosure of which is hereby incorporated by reference in its entirety.

FIELD OF THE DISCLOSURE

The present disclosure relates to methods for reducing the symptoms of neurodegenerative disease in a human.

BACKGROUND

Dystonia remains on the spectrum of Parkinsonism1, which has commonality with Alzheimer's Disease as both disorder entorrhinal cortex.

I discovered that Conjugated Linoleic Acid (K-CLA) has extraordinary anti-microbial capacity against gram positive and negative bacteria as well as fungi including *Malassezia, Aspergillus*, and *Candida*. Conjugated Linoleic Acid (CLA) is a generally recognized as safe nutritional supplement (not a drug) accepted by the CFSAN with the FDA and sold in the US.

There is a long history and documentation for safety with respect to pregnancy, children, and environment. It has been shown that autopsied Parkinson/Alzheimer's-Diseased brains contain DNA of bacteria and fungi present in skin and mucous membranes. This includes *Malassezia* and *Aspergillus*, abundantly present on skin and nasal-pharynx. Additionally, microbial origins of neurodegenerative diseases Dystonia, Parkinsonism, Alzheimer's Disease, and Amyotrophic Lateral Sclerosis have been proposed, but the microbial origin of Neurodegenerative diseases has not become accepted. There has not been a fully identified a mechanism for microbial skin elements to find their way into brains to initiate the neuroinflammatory response known as Parkinsonism/Alzheimer's Disease or a way to alter this process.

It may be desired to provide methods for reducing neurodegenerative disease by reducing the microbial origin of Neurodegenerative diseases.

SUMMARY

In one aspect of the present disclosure, a method of reducing the symptoms of neurodegenerative disease in a human is provided. The method comprises applying to the human a solution or salve to at least one of the skin, the mouth, the nasal cavities, the lungs, the eyes, or the vagina of the human. The applied solution or salve comprises an effective amount of an isomerized or conjugated linoleic acid cation salt having a conjugated diene for at least a measurable improvement in the movement or mental acuity of the human. The conjugated diene has a structure of —C=C—C=C— and the measurable improvement in the movement or mental acuity of the human is within 4-6 weeks of the applying of the solution or salve.

In another aspect of the present disclosure, a method of making the isomerized or conjugated linoleic acid cation salt in the solution or salve for the reducing of the symptoms of the neurodegenerative disease in the human is provided. The method comprises saponifying an oil containing linoleic acid with excess metal cations to yield a mass. The saponified mass is then heated to a temperature between about 220 and about 400 degrees F. and the mass is dissolved in water.

In a further aspect, the method of reducing the symptoms of neurodegenerative disease in a human comprises measuring the reduction of the symptoms of the neurodegenerative disease the human. The measuring comprises an initial measuring of a rotation of a wrist of the human, prior to the applying the solution or salve, and a subsequent measuring of the rotation of the wrist of the human, after the applying the solution or salve. The measuring of the rotation of the wrist comprises grasping a handle, rotating the wrist and thereby moving a push tool, the push tool moves a first marker and a second marker, the location of the moved first marker measures the maximum rotation of the wrist in a first direction and the location of the moved second marker measures the maximum rotation of the wrist in a second direction.

In yet another aspect, a wrist rotation measuring device is provided. The wrist rotation measuring device comprises a handle, a rod extending from the handle, a cylinder disposed with the rod, a string or cord extending through the cylinder and about a plurality of pulleys, and a push tool disposed with the string or cord. The push tool is configured and disposed to move the first and the second markers upon the rotating of the wrist in the first direction and in the second direction.

BRIEF DESCRIPTIONS OF THE DRAWINGS

The foregoing and other features of this disclosure will become more fully apparent from the following description and appended claims, taken in conjunction with the accompanying drawings and examples. Understanding that these drawings depict only several embodiments in accordance with the disclosure and are, therefore, not to be considered limiting of its scope, the disclosure will be described with additional specificity and detail through use of the accompanying drawings, in which:

Figure 4A:
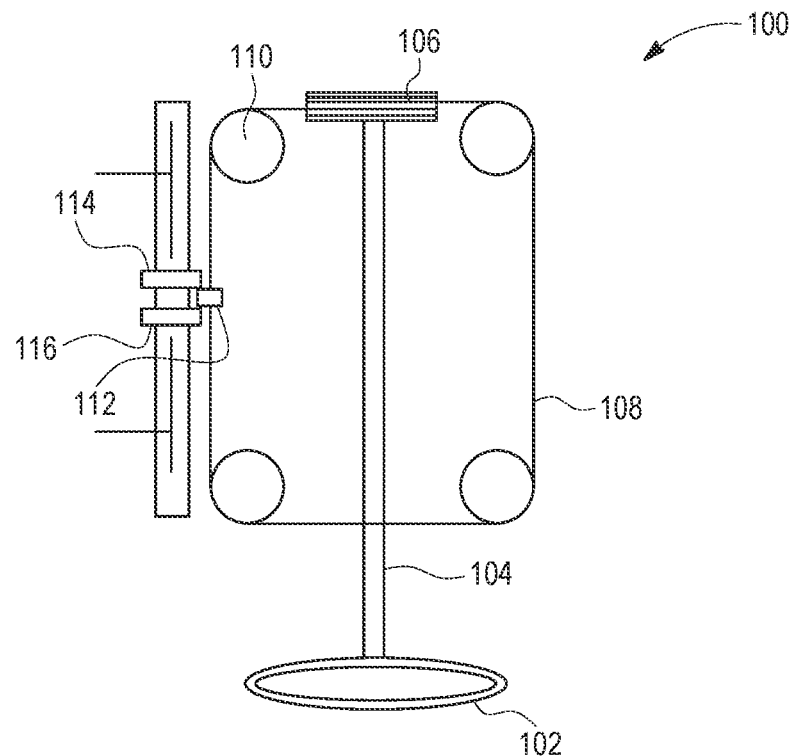
Figure 4B:
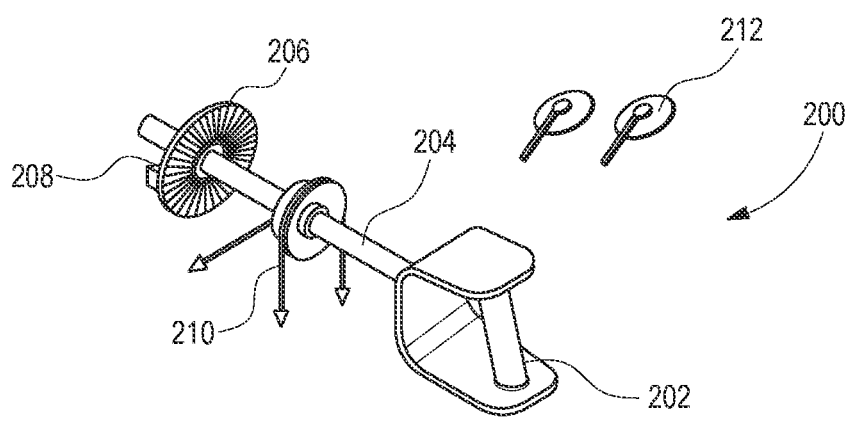
Figure 4C:
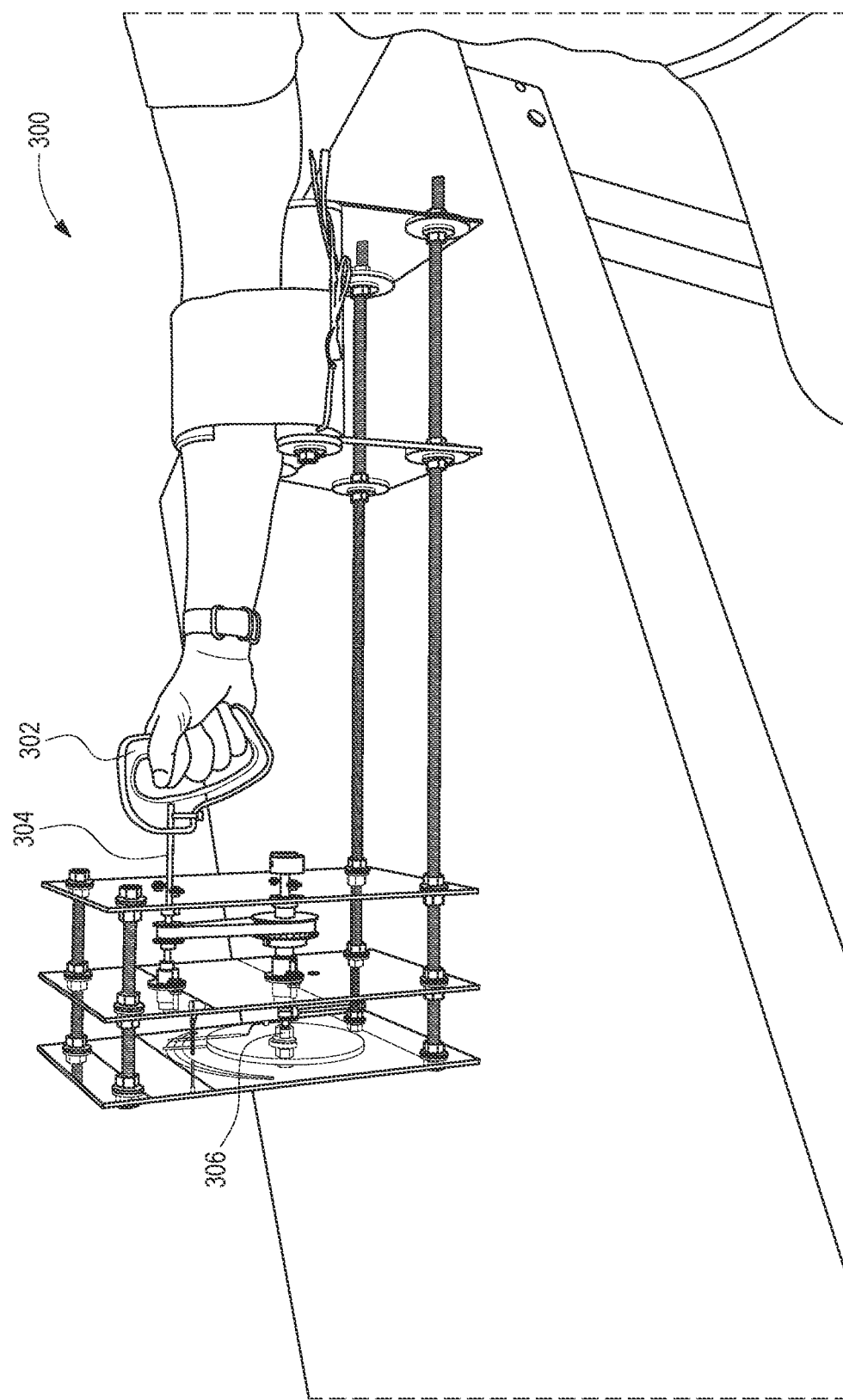
Figure 4D:
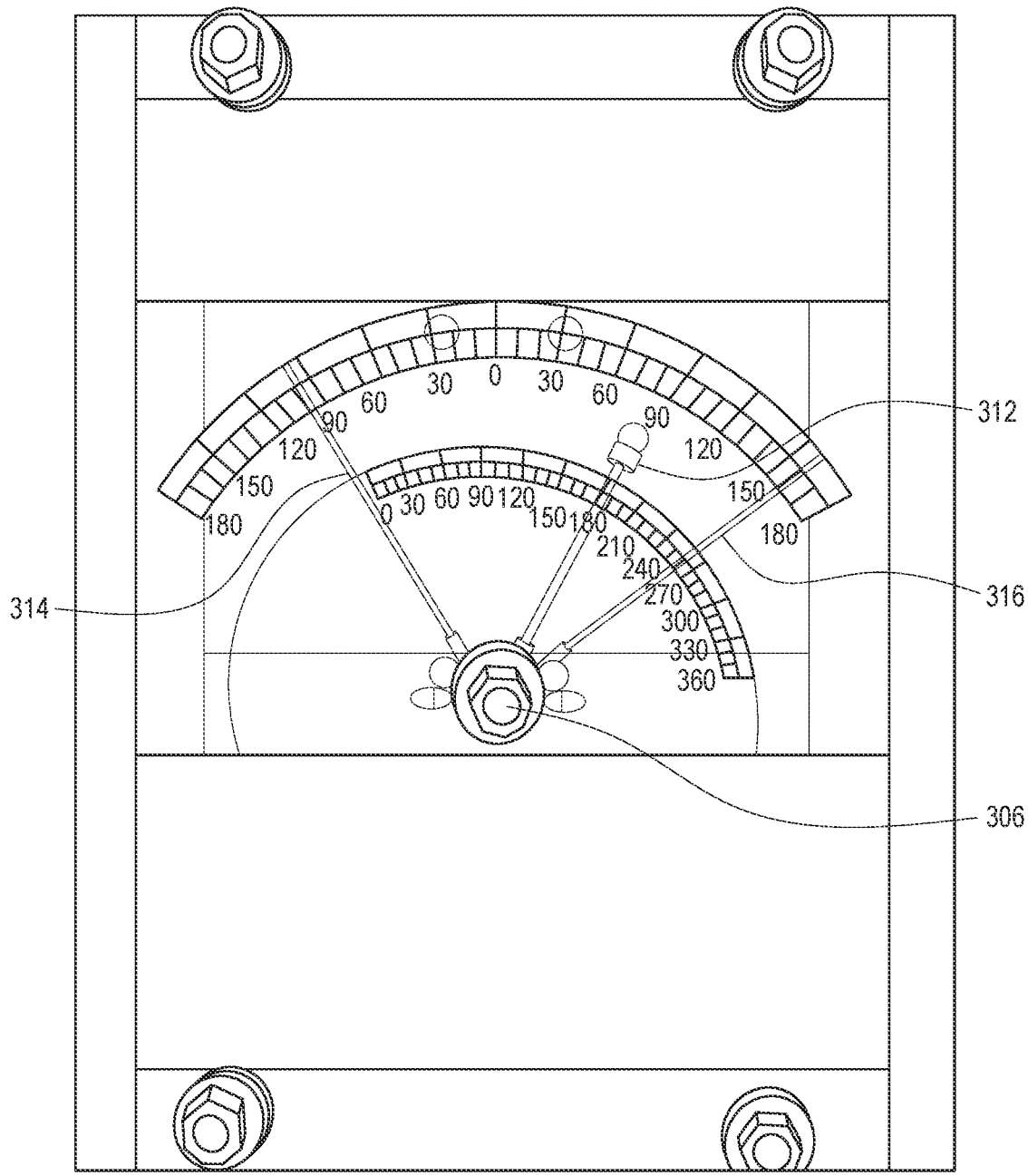

FIG. 4*a* schematically shows a rotational measurement tool configured for measuring effects of the presently disclosed treatment;

FIG. 4*b* illustratively shows a rotational measurement tool configured for measuring effects of the presently disclosed treatment; and FIGS. 4*c* and 4*d* illustratively show an alternative rotational measurement tool configured for measuring effects of the presently disclosed treatment.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

In at least one embodiment of the present disclosure, a method of amelioration of dystonia/parkinsonism with skin application of potassium linoleate (isomerized) is provided. I discovered that Conjugated Linoleic Acid (K-CLA) has extraordinary anti-microbial capacity against gram positive and negative bacteria as well as fungi including *Malassezia*, *Aspergillus*, and *Candida*. It has been shown that autopsied Parkinson/Alzheimer's-Diseased brains contain DNA of bacteria and fungi present in skin and mucous membranes, this includes *Malassezia* and *Aspergillus*, abundantly present on skin and nasal-pharynx. Additionally, microbial origins of neurodegenerative diseases Dystonia, Parkinsonism, Alzheimer's Disease, and Amyotrophic Lateral Sclerosis have been proposed. However, the microbial origin of Neurodegenerative diseases has not become accepted. There has not been a fully identified a mechanism for microbial skin elements to find their way into brains to initiate the neuroinflammatory response known as Parkinsonism/Alzheimer's Disease or a way to alter this process.

Nerves, with their well defined internal transport conduits, may be the missing link between skin and brain. For example, nerves can transport rabies into the brain; herpes virus travels from sensory ganglia to skin to cause lip ulcers and zoster. The capacity of nerves to transport large proteins and even viruses is used every day in neuroanatomy departments to study the intraconnections of brain.

Potassium Isomerized Linoleate (PIL) has cross-kingdom anti-bacterial and anti-fungal efficacy sufficient to satisfy the United States Environmental Protection Agency requirements for hospital disinfection (David G. Changaris and Carenbauer 2022). Several "silos" of information have interdependent significance in this context. The prospect of a microbiological origin of neurodegenerative diseases has evolved over decades (Vigasova et al. 2021; Munoz-Pinto, Empadinhas, and Cardoso 2021). Of late, some have demonstrated by PCR-DNA amplification the DNA of a growing number of microbes in the autopsied brains of those with Parkinson's Disease (Alonso et al. 2018). These findings have renewed interest in this largely ignored possibility. The challenge for this perspective is the paucity of clear evidence of central-nervous-system invasion by putative microbes such as *Malassezia* (Pisa et al. 2015; Munoz-Pinto, Empadinhas, and Cardoso 2021).

Two additional less well-known "silos" of generally accepted scientific observations support the likelihood that dermal microbes can and do contribute to the clinical picture thought to be a primary neurodegenerative process. The first is that the list of species, whose DNA is present in the brains of those with neurodegenerative diseases, corresponds to those present within our epidermal-dermal microbiome (Pisa, Alonso, and Carrasco 2020). The second is that neurons possess and actively utilize the talent to absorb and transport complex proteins and DNA into the central nervous system (Anderson, Mitchell, and Mayor 1980). Indeed, not only does rabies virus enter the central nervous system through the neuron (Piccinotti and Whelan 2016), but neurotoxins such as ricin can be delivered into the brain by neuronal uptake with metabolic consequences (Tang, Tsai, and Hammerschlag 1994).

Fungi, in particular, have the capacity to maintain immunologic stealth (Kashem and Kaplan 2016). Specifically, *malassezia* has been linked to Parkinson's disease (Pisa, Alonso, and Carrasco 2020). Numerous skin conditions evolve with Parkinson's Disease, the most notable, Seborrhea, is caused by *malassezia* (Arsic Arsenijevic et al. 2014; Ravn Jørgensen, Thyssen, and Egeberg 2017). Despite the presence of *malassezia* and other microbial DNA in brain, active infections of the brain have not been accepted as the basis of the widespread neurodegeneration facing aging humans worldwide. While we may not be capable of identifying which microbe(s) in the skin may be linked to the reported reduction in motor signs of neurodegenerative diseases, the broad spectrum anti-fungal and anti-bacterial capabilities of Potassium Isomerized Linoleate provides the microbial relationship where antibiotics against bacteria or anti-fungals alone would not.

The complex innervation of the hair follicle offers somatic and visceral nerves to transport into the central nervous system both small chemicals and large molecular weight structures such as DNA (Anderson, Mitchell, and Mayor 1980; Bentivoglio et al. 1980; Prior et al. 2017; Xu et al. 2020). Neuronal innervation of the erector pili muscles that cause the "hairs to stand on end" link to our emotional centers. Somatic sensory neurons for both light touch and pain are present. Visceral efferent and afferent neurons regulate sweat glands. The hair follicle may offer microbes a strategic entry to spread throughout our epidermal-dermal lymphatics (Schneider, Schmidt-Ullrich, and Paus 2009). These capillary lymphatics do not have valves, so, unfettered direct extension and gravity spread can occur. Within the hair follicle microbes may begin saprophytic nutrition with sebaceous glands, muscle, and the full array of neuronal elements.

Of parallel relevance, some mycologists view of fungi that can create mycelial networks with a distributed intelligence and note that fungi can interact with the environment, even managing nutrition with appearance of sentience (Fukasawa, Savoury, and Boddy 2020). The well-known interaction by *ophiocordyceps* within tropical ants (de Bekker 2019; Arsic Arsenijevic et al. 2014) indicate that this fungus can cause an ant to change social behavior, climb a nearby plant overhanging the nest, clamp onto the plant with its pincers, and die. Then, the *ophiocordyceps* rains infectious spores onto the ant hill below (Hywel-Jones 1996). Similar near sentient behavior of fungi in particular presents in other species (Libersat, Kaiser, and Emanuel 2018) where the host engages in behaviors benefiting the fungus. Finally, the presence of mind-altering chemicals within fungi has some concerned that ants may not be the only victim of mind and behavior alterations caused by fungi (Lovett, St. Leger, and de Fine Licht 2020). The incidence of Alzheimers' Disease in Finland is both greater than other developed nations and more aggressive. Some have suggested mycotoxins or specific toxins from cyanobacteria prevalent in Finnish waters (Eiser 2017). While direct invasion of the brain does not occur early with *ophiocordyceps* infection, the infected ant engages in confused social behavior that favors the fungus. This suggests an effect remotely (Fredericksen et al. 2017).

*Malassezia*, the most prevalent microbe in our skin microbiome, infects humans worldwide matching or exceeding the age-related prevalence of neurodegenerative diseases (Gupta and Kohli 2004). This fungus also generates a biofilm making its subclinical persistence common. As the lifelong growth of *malassezia* continues, it or other seemingly commensal microbes may trigger debilitating neurodegenerative disease after decades of growth in the skin. If this yeast-fungus can engage in quorum sensing as does its sister *candida* (Kashem and Kaplan 2016), at some density it may begin to secrete neurotoxins within the skin. Neurons can transport these into the brain. In neurodegenerative states, the debilitated with loss of mental acuity causes other humans to render close physical support. From this perspective, a potential fungal-life cycle might involve the aging victim of Parkinsonism. Those with Parkinson's Disease suffer with seborrheic dermatitis and may infect those providing support to renew the cycle. This loosely parallels the observations concerning *ophiocordyceps*-induced-behavioral changes in the ant (Libersat, Kaiser, and Emanuel 2018).

Potassium salt of Isomerized Linoleic acid (PIL) has biocidal capacity against at least four *malassezia* species (D. G. Changaris and Sullivan 2019), *candida, aspergillus* and many gram positive and negative bacteria. Moreover, as most plant oil salts, PIL has powerful surfactant capacity which may penetrate immunological masks fungi possess. It is shown herein that topical biocidal PIL can alter clinical dystonia and dense monoparetic Parkinsonism, Alzheimers Disease, and Amyotrophic Lateral Sclerosis. All three diseases have been shown to have isolatable DNA in autopsied brain. The present disclosure provides a method to interfere with the clinical expression of movement disorders and may provide both investigative and therapeutic options.

In at least one embodiment of the present disclosure, a method of reducing the symptoms of neurodegenerative disease in a human is provided. The method comprises applying to the human a solution or salve to at least one of the skin, the mouth, the nasal cavities, the lungs, the eyes, or the vagina of the human. The applied solution or salve comprises an effective amount of an isomerized or conjugated linoleic acid cation salt having a conjugated diene for at least a measurable improvement in the movement or mental acuity of the human. The conjugated diene has a structure of —C=C—C=C— and the measurable improvement in the movement or mental acuity of the human is within 4-6 weeks of the applying of the solution or salve. For example, a salve may be applied to at least one of the skin, the mouth, the nasal cavities, the lungs, the eyes, or the vagina of the human. The neurodegenerative disease being treated may be one of Dystonia, Parkinsons's, Alzheimers, and Amyotrophic Lateral Sclerosis.

In at least one other embodiment, the applied conjugated diene consists essentially of cis-9, trans-11 conjugated linoleic acid. The applied conjugated diene may be substantially void of trans-10, cis-12 conjugated linoleic acid. For example, the applied solution or salve may consist essentially of cis-9, trans-11 conjugated linoleic acid and be substantially void of trans-10, cis-12 conjugated linoleic acid. The solution or salve may comprise at least one of water, amino acid, and alcohol. In at least one further embodiment, the solution or salve comprises cations at least at a molar equivalent to the conjugated diene in the solution or salve. For example, the cations may be at a molar ratio of the cations to the conjugated diene between about 1:1 and 5:1.

In at least one embodiment, the cations are selected from the group consisting of lithium, sodium, potassium, rubidium, and combinations thereof. For example, the cations may comprise potassium. In at least one other embodiment, the solution or salve comprises a concentration of the conjugated diene between about 0.1 millimolar and about 500 millimolar. For example, the solution or salve may comprise a concentration of the conjugated diene between about 0.2 millimolar and about 60 millimolar.

A provided device may be configured for measuring the angle of movement and/or torque of the human limbs, head and spine correlating with surface or deep electromyography or brain electrical activity including electroencephalography and somatosensory evoked potentials.

This may include surrounding the limb, head and/or spine with mechanical or electromagnetic receptors on or adjacent to the limb, head or spine while the limb moves actively against resistance either variable or static and correlating with surface or deep electromyography or brain electrical activity include electroencephalography and somatosensory evoked potentials. The device may provide for a system for functional magnetic resonance imaging.

A method of reducing the symptoms of neurodegenerative disease in a human may comprise making an initial measuring of a rotation of a wrist of the human, prior to the applying the solution or salve, and a subsequent measuring of the rotation of the wrist of the human, after the applying the solution or salve. The measuring of the rotation of the wrist comprises grasping a handle, rotating the wrist and thereby moving a push tool, the push tool moves a first marker and a second marker, the location of the moved first marker measures the maximum rotation of the wrist in a first direction and the location of the moved second marker measures the maximum rotation of the wrist in a second direction.

A device configured to measure the amelioration is also provided. The measuring of the rotation of a rotation of a wrist may be performed with a wrist rotation measuring device for measuring the amelioration of the neurodegenerative disease. The wrist rotation measuring device may have a handle, a rod extending from the handle, a cylinder disposed with the rod, a string or cord extending through the cylinder and about a plurality of pulleys, and a push tool disposed with the string or cord. The push tool is configured and disposed to move a first and a second marker upon the rotating of the wrist in the first direction and in the second direction.

The device has a wrist rotation mechanism is configured to quantify improvements in movement disorders. The measuring device may be configured for measuring the force of rotation, coupled with the activation of forearm muscles by surface electromyography. The device has been developed using Arduino boards, strain gauges, and surface EMG technology and may be configured for physician-in-office use for the early diagnosis of Dystonia/Parkinsonism.

FIG. 4a schematically shows a rotational measurement tool 100 configured for measuring effects of the presently disclosed treatment. FIG. 4a shows the schematic of rotational measurement tool for measuring wrist rotation in both arm bent and extended. During the measurement, it is easy to discern components of arm movement related to extended wrist rotation as separable from shoulder rotation through scapular movement. Careful observation can easily identify 20-180 degrees wrist rotation due to shoulder (scapular movement), an additional 90 degrees of proximal humeral rotation within the glenoid capsule, at the extreme of internal wrist rotation wrist flexion further enhances the range of motion. This capacity for scapular, proximal humeral and wrist movement may be enhanced with training such as ballet or movement study. If mental capacity is sufficient these "trick" movements can be limited so the subject provides the wrist rotation accurately. The subject sits facing the device and the appropriate arm extended. External rotation of the wrist normally ranges 90-120 degrees and internal rotation ranges 170-240 degrees. These measures recorded separately document clinical course. The influence of the scapula, humeral, and wrist rotation often comprises a significant component of the measures. The decision to separate these movements is a clinical one. In late dystonia, the shoulder may be incapable of these movements making the wrist rotation an easy clinical observation.

The extended wrist rotation measurement device may hay have gears with monitoring olecranon position to determine isolated wrist rotation. The measuring device may be configured for both external and internal rotation of the wrist with active olecranon displacement. As the olecranon moves, the wrist rotates gears separately in both external and internal rotation relative to the olecranon position. Recently, technology has developed with three-dimensional inertial capacity and gravity. Two or more such devices may be configured to provide the relative wrist rotation and arm movement.

The presently disclosed method may comprise an initial measuring of a rotation of a wrist of the human, prior to the applying the solution or salve, and a subsequent measuring of the rotation of the wrist of the human, after the applying the solution or salve. The measuring of the rotation of the wrist comprises grasping a handle, rotating the wrist and thereby moving a push tool, the push tool moves a first marker and a second marker, the location of the moved first marker measures the maximum rotation of the wrist in a first direction and the location of the moved second marker measures the maximum rotation of the wrist in a second direction.

Wrist rotation measuring device 100 has a handle 102. A rod 104 extends from handle 102 and a cylinder or actuator 106 is disposed with the rod 104. A string or cord 108 is in communication with actuator 106 and is configured and disposed to move about a plurality of pulleys 110 upon activation of actuator 106, with the rotation of the wrist. A push tool 112 is disposed with string or cord 108, wherein push tool 112 is configured and disposed to move a first marker 114 and a second marker 116, upon the rotating of the wrist in a first direction and in a second direction.

FIG. 4b illustratively shows a rotational measurement tool 200 configured for measuring effects of the presently disclosed treatment. Wrist rotation measuring device 200 has a handle 202. A rod 204 extends from handle 202 and an actuator 206 is disposed with the rod 204. An angle measure 208 is configured and disposed to measure the angular movement of actuator 206 upon the rotation of handle 202. An electromyograph 212 may be applied to the patient to assess the health of patient's muscles and the nerve cells that control them. A torque measurer 210 may be in communication with rod 204 or actuator 206.

FIGS. 4c and 4d illustratively show rotational measurement tool 300 configured for measuring effects of the presently disclosed treatment. Wrist rotation measuring device 300 has a handle 302. A rod 304 extends from handle 302 and is in communication with actuator 306. Actuator 306 is configured and disposed to move or rotate upon rotation of handle 302. A push tool 312 is disposed with actuator 306 and is configured and disposed to move a first marker 314 and a second marker 316, upon the rotating of the wrist in a first direction and in a second direction.

We have identified a novel simple safer method to generate high purity cis-9, trans-11 conjugated linoleic acid octadecadienoic acid or linoleic acid (isomerized), or commonly known as rumenic acid, the naturally occurring conjugated linoleic acid. Multiple publications for the manufacture of isomerized linoleic acid report general methods incorporating metallic catalysts, elevated pressure, sequestration from oxygen, and high temperature. The published processes often require temperatures sufficiently high making uniform heating of large volumes of oils such as safflower seed oil an existential risk to keep below the ignition temperature of the oil.

We have discovered that heating a saponified oil containing linoleic acid with excess metal cations with microwaves provides high purity cis-9, trans-11 conjugated linoleic acid octadecadienoic. We have also discovered that by changing the parameters of microwave energy transfer we can produce different isomers of conjugated octadecadienoic acid. Surprisingly, this reaction can be carried out in room air and the finished product salt is stable for months or longer in a low humidity environment while sequestered in oxygen permissive contains such as wood paper or polypropylene jars.

Removal of the cations with aqueous solubilization and addition of strong acids such as citric or phosphoric acid will produce >90% pure cis-9, trans-11 octadecadienoic acid. While the microwaved product powder may be stored in ambient low moisture environment, the resulting oil may require sequestration from oxygen to prevent spoiling.

Current food labeling standards within the United States indicate that food "Organic" status remains intact with the addition of water, monovalent cations such as potassium or sodium, microwaves, citric acid, and/or phosphoric acid. Hence this method may allow for the synthesis of rumenic acid from organic oils while preserving the parent oil's legal definition for organic food labeling.

The process begins with saponification of an oil containing linoleic acid with excess metal cation (molar ratio with fatty acid 1.1-8.0, preferably 1.5-4.5, ideally 2.5-3.5). The saponified mass may be exposed to microwaves in ambient or reduced oxygen free environment. Changing the glycerin or alcohol may alter the rate of volume expansion and temperature required to drive the desired reaction to completion.

The formation of rumenic acid with the presently disclosed method does not require the addition of any further glycerin or alcohol beyond that released during saponification. In general the saponified mass increases in temperature (220-400 degrees F., preferably 230-350 degrees F., ideally 240-280 deg F.) during the expansion (5-50-fold initial volume, preferably 8-25 fold initial volume, ideally 12-20 fold initial volume). The finished product, expanded saponified mass, falls in temperature and does not increase in temperature with further exposure to the microwave. This lends a substantial safety factor in defining the desired precise application of this method.

In at least one embodiment, the isomerized or conjugated linoleic acid cation salt in the solution or salve is made by saponifying an oil containing linoleic acid with excess metal cations to yield a mass. The saponified mass is heated to a temperature between about 220 and about 400 degrees F. and expanded. The expanded saponified mass is then dissolved in water. The heating of the saponified mass is preferably heated with microwaves.

In at least one embodiment, the heating comprises microwaving the saponified mass to a temperature and for a period of time to increase a volume of the saponified mass to at least 5 times its initial volume. The saponifying of the oil may comprises saponifying safflower oil and/or the cations may comprise potassium. For example, in at least one embodiment the oil comprises safflower oil, the cations comprise potassium, and the saponified mass comprises the oil and the cations at an oil to cation weight ratio of about 7 to 3.

In at least one embodiment, the method comprises adding squalane to the saponified mass dissolved in water and mixing and mechanical high shearing and thereby forming an emulsion.

EXAMPLES

Example 1

Over the years, I observed progression of dystonia of a patient. The symptoms of the neurodegenerative disease were observed in the right arm with intensifying muscular pain. An extended forearm wrist rotation was used to identify and measure progression of dystonia. A normal human can rotate the wrist of the fully extended arm more than 270 degrees. The patient was falling to 200 degrees with increasing pain in the opposing forearm muscles.

Last spring, I applied a salve of K-CLA, potassium-conjugated linoleic acid, to potentially kill the microbial residents in the skin causing the dystonia. Most of the dystonic symptoms were resolved.

Example 2

Dystonia with Left Hand Tremor, Reduced Extended Wrist Rotation and Painful Forearm Muscles.

This 72-year-old male presented with right arm dystonia after complaints of hand incoordination worsening with vibration. Muscle tenderness and loss of range of motion of extended-wrist rotation defined the clinical diagnosis confirmed by pattern EMG (Nicolet) within a university neurology clinic. The Potassium safflowerate of Example 11 as a salve. Within hours improvement in his range of motion of his extended wrist rotation. The hand tremor improved minimally. Subsequent applications continued to result in extended wrist rotation, forearm muscle tenderness and improving hand tremor. Erythema and superficial lymphatic disruption were eliminated with spacing of dosing and application of Example 12. The improved capacity including reduction in hand tremor has continued with application of Example 10 and 11 application every 2-7 days. Adding the oral intake of 2 capsules of Example 13 was associated with further improvement in strength and coordination.

Example 3

Right-Handed Hemiparetic Male with Parkinsonism with Dystonia and Tremor

This 54-year-old male presented with left hemiparetic neglect, reduced finger fine motor capacity, flat affect, tremor, and reduced extended arm wrist rotation and loss of shoulder extension and abduction. The diagnosis of Parkinsonism on clinical grounds was confirmed at a major hospital chain neurology clinic. With application of the potassium safflowerate (isomerized) in Example 11 to skin along with the ingestion of isomerized safflowerate capsules, he improved tremor and his extended-wrist-rotation range. The range of motion of the shoulder and arm improved over weeks to months. The initial erythema and disruption of the superficial lymphatic plexus resolved with spacing of applications and continuing use of the emollient in Example 12. His extended wrist rotation range measured 60 degrees initially; by six months this approached 200 degrees. At 3 months he could extend his shoulder quickly to 180 degrees (initially slowly to 60 degrees.) This functionality continues to be maintained over 15 months of intermittent applications of salve and ingestion of isomerized safflowerate.

Example 4

Right Hand Tremor Reduced Extended Wrist Rotation and Head Rotation in Dystonia Parkinsonism.

This 62-year-old male presented while on Sinemet prescribed by a major hospital chain neurology clinic for Parkinsonism. His tremor was reduced with the Sinemet but he continued to have painful writing and difficulty signing his signature. He also had reduced head rotation with painful limitation.

Two applications of the Example 12 to the right arm, shoulder, C2-C5 dermatomes (bilaterally only in the upper torso from 4 inches into the hair line to the nipples, bilaterally) after 30-60 minutes resulted in improved right hand tremor, pain, wrist rotation, and head rotation. This individual stopped his Sinemet, continued every other day application of the Example 12 and oral intake of isomerized safflowerate. Improvement has maintained for 4 months, with rare intermittent right-hand tremors after a day of heavy farming.

Example 5

Right Hand-Arm Restless Dystonia Parkinsonism

This 44-year-old woman sustained the onset of right arm dystonic Parkinsonism several months after a traumatic brain injury. This was treated with selegiline as tolerated without significant improvement. She was treated by two applications of the Example 12 to the right arm, shoulder, C2-C5 dermatomes (only in the upper torso from 4 inches into the hair line to the nipples, bilaterally) after 30-60 minutes resulted in improved right hand tremor, pain, wrist rotation, and head bobbing. Personal life issues prevented further applications.

The patient was instructed to rotate, extend and open her hand while she was actively having right hand-arm Parkinsonism tremors. She was unable to either rotate her wrist or open her hand voluntarily initially as shown on the left picture so she attempts to force it open with her left hand. The patient was treated with application of the salve over her right arm, subocciput, and upper torso bilaterally. One hour later post upper body and arm application her tremor had subsided substantially, and she was able to open her hand.

Example 6

Amyotrophic Lateral Sclerosis of Several Years Duration.

A 62-year-old woman with progressive Amyotrophic Lateral Sclerosis presented with her right arm and hand without voluntary movement and normal sensation. She was concerned about her left-hand losing coordination and capacity. She had loss of extended wrist rotation on her left arm. The right arm could not be tested due to its essentially paralyzed state. Two applications of the Example 12 to the left arm, shoulder, C2-C5 dermatomes (only in the upper torso from 4 inches into the hair line to the nipples, bilaterally) after 30-60 minutes resulted in measurable improved left arm wrist rotation and perceived mobility as well as head rotation. This has been maintained with continued use of the salve of example 12.

Example 7

Alzheimer's Syndrome with Parietal Atrophy

A 62-year-old woman presented with failure to thrive (from 108 lbs to 88 lbs), progressive anxiety, and difficulty performing her duties related to her business. MRI showed extensive atrophy of Parietal and Temporal occipital lobes consistent with posterior cortical atrophy of Alzheimer's. She was treated with applications of Example 11 and 12 to her back (18% body surface area). She showed improvement in mentation and energy after 3-10 days. Coupled with physical therapy she showed continuing improvement with the incorporation of 1 g isomerized safflowerate into her diet. She regained her weight over 2-3 months and returned to her workload involving travel by air after 6 months. She maintains her capacities at a pre-morbid level by her report at 16 months treatment with salve application, example 12, to different 9-18% body surfaces. She also engages in mindfulness, somatic therapy, and wellness activities.

Example 8

Alzheimer's Syndrome with Hallucinations and Loss of Fine Motor Capacity

A 69-year-old male was arrested/detained two thousand miles from his family. When taken into custody he was disoriented and unable to drive any further. His hallucinations were of people at a distance, without auditory components or familiar people who would simple be in the room with him. He was returned to his home with his family and treated with memantine. He started surface application of Example 12 every other day over rotating areas of his skin, about 40% of his body alternating upper and lower body. And he ingested 1-gram isomerized safflowerate daily. He had been a professional drummer but could not hold and play his drum sticks usefully, initially. Over six months his hallucinations regressed to happening for a day every two months. Running out of his emollient for a week or two was associated with increasing hallucinations, restarting reduced hallucinations over 5-10 days. The capacity to play with his drumsticks with syncopated beat patterns continues to improve. He is able to self-care, manage his food, and practice his drums independently with oversight at 15 months from his incarceration.

Example 9

Five Patients Having Dystonia with Traumatic Brain Injury.

Five patients aged 42-67 using recorded videos of hand movement Dystonia/Parkinsonism before and after application of Example 12 for 5-10 days. Four had bilateral symptoms. Using video capture to measure the rotation of their wrists before and after application of the PIL0.1-120 0. The paired T analysis of these 5 patients showed improvement (p<0.05). This improvement has been sustained with intermittent continuing application of the salve to the skin of the forearm and shoulder for 3 months.

Subsequently, I have recorded videos of hand movement in patients with Dystonia/Parkinsonism before and after similar treatment. Several had bilateral symptoms. Video capture was used to measure the rotation of their wrists before and after application of the K-CLA 0.1-12%. The paired T analysis of most 5 patients showed improvement (p<0.05). This improvement has been sustained with intermittent continuing application of the salve to the skin of the forearm and shoulder. One on the left below is an architect who felt his capacity to draw has improved with this intervention. Application of a broad spectrum antimicrobial with profound antifungal capacity can reverse symptoms of Dystonia/Parkinsonism.

Figure 1:
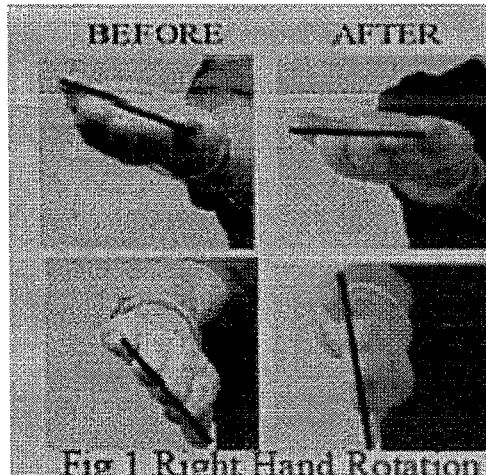
FIG. 1 shows an illustrative example of wrist rotation, before and after the application of the solution or salve in accordance with the presently disclosed method.
Figure 1:
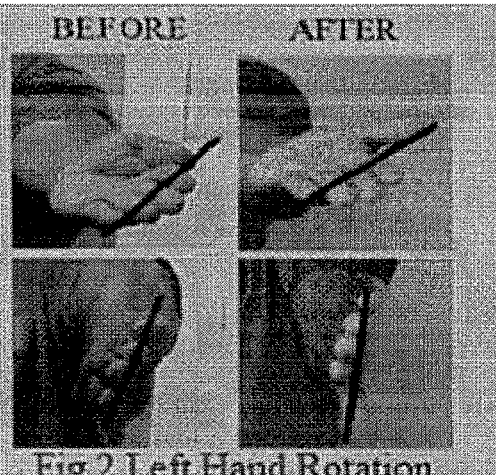

A measurable improvement was exhibited in extended wrist rotation within weeks while applying K-CLA as salve. FIG. 1 shows examples of wrist rotation, before and after the application of the solution or salve, of two of the five patients. A first patient exhibited about a 20% increase in external wrist rotation as shown in the two upper left photographs. As shown in the two pictures in the lower left, the same patient exhibited about a 30% increase in internal wrist rotation. A second patient exhibited about a 10% increase in external wrist rotation as shown in the two upper right photographs. As shown in the two pictures in the lower left, the second patient exhibited about a 20% increase in internal wrist rotation.

Example 10

Figure 2:
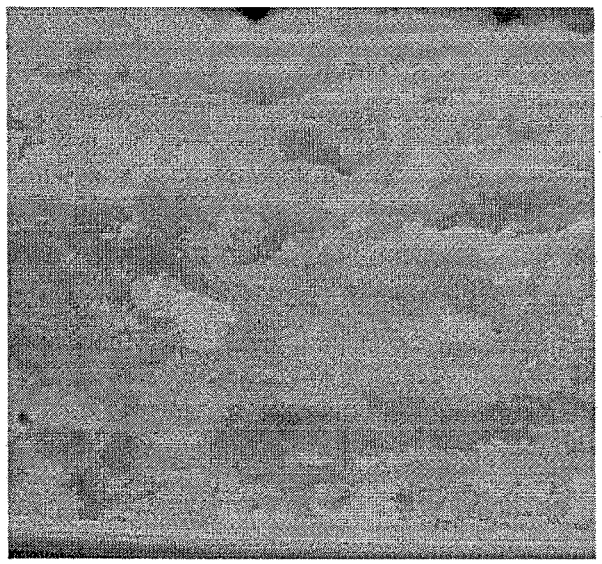
FIG. 2 shows a cut surface of expanded mass of saponified safflowerate in accordance with the presently disclosed method of making the isomerized or conjugated linoleic acid cation salt in the solution or salve.
Figure 3:
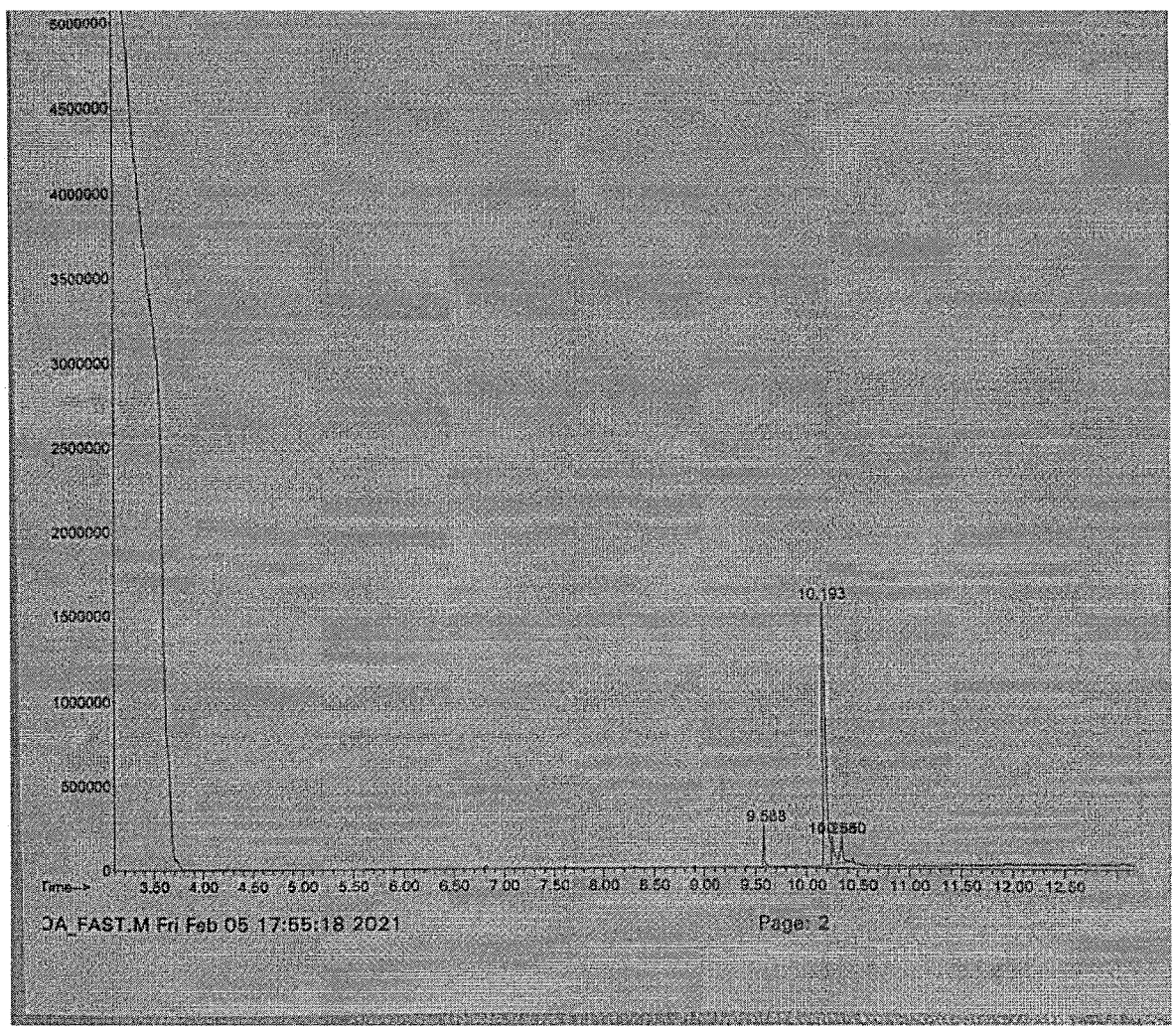
FIG. 3 shows a Chromatography Mass Spectrograph mass of the saponified safflowerate made with the presently disclosed method of making the isomerized or conjugated linoleic acid cation salt in the solution or salve.

Manufacture of CLA Cis-9, Trans-11 Octadecadienoic Acid
  Mixing Water 2.5 kg, Potassium Hydroxide 3 kg, and Safflower Oil 7 kg
  Microwave @2.45 gHz until reaction complete as evidence by drop in surface temperature below 200 degree F.
  FIG. 2 shows a cut surface of expanded mass of saponified safflowerate after microwaving completed. The saponified safflowerate mass was expand about twenty times its original height upon being heated with microwaves.
  Dissolve in water, add acid to neutralize and remove surface oil as CLA. Wash and dehydrate CLA with water under nitrogen or vacuum.
  FIG. 3 shows a Chromatography Mass Spectrograph with retention time consistent with >90% substantially pure cis-9, trans-11 octadecadienoic acid of post-microwaved salt dissolved in water and titrated to pH2 with phosphoric acid 80%. The oil separated and washed with water and steam prior to this study. CLA esters (methyl or ethyl esters) or oil samples were used to prepare fatty acid methyl esters, FAME ("Comparison of commercial supplements containing conjugated linoleic acids", Liangli Yua, Dwayne Adams, Bruce A. Watkins, Journal of Food Composition and Analysis 16 (2003) 419-428). The analysis was performed by Boston University, Chemistry Department, CIC Mass Spec, 590 Commonwealth Avenue, Boston MA. Peaks were exhibited at 9.588, 10.193, 10.258, and 10.350 minutes. Trans-10, cis-12 linoleic acid isomers were not identifiable.

Example 11

Aqueous solution of potassium safflowerate (isomerized). The post microwaved and sifted powder of Example 10 was solubilized in purified water (16% by weight). This produced a pale-yellow viscous solution.

Example 12

10% squalane (olive) was added to the pale-yellow viscous solution of Example 11 with mechanical high shearing, which created a soft white to pale yellow emulsion.

Example 13

The resulting powder from Example 10 was placed within cellulose 0 capsules, final weight 0.7 g/capsule by standard packing for oral ingestion.

The present disclosure may provide extraordinary potential to impact neurodegenerative diseases far beyond the improvement of the symptoms of mild dystonia. One of the patients now has improving acute hemiparetic Parkinsonism with both strength and agility due to this salve, having refused conventional medications. Another with early Alzheimer's disease and demonstrated cortical atrophy has shown clinical improvement in mental acuity and emotionality with skin application of K-CLA. Both had intense skin reactions consistent with significant underlying microbial skin infections involving the superficial and deep lymphatics.

Presently disclosed is a method of reducing the symptoms of neurodegenerative disease in a human comprising: applying to the human a solution or salve to one of the skin, the mouth, the nasal cavities, the lungs, the eyes, or the vagina of the human, wherein the applied solution or salve comprises an effective amount of an isomerized or conjugated linoleic acid cation salt having a conjugated diene for at least an improvement in the movement and/or mental acuity wherein the conjugated diene has a structure of —C=C—C=C—.; and wherein the improvement in the movement and/or mental acuity is within 4-6 weeks of the applying of the s solution or salve.

In at least one embodiment, the disease is, Dystonia, Parkinsons's Disease, Alzheimers, or Amyotrophic Lateral Sclerosis. The solution may further comprise at least one of water, amino acid, and alcohol. The solution or salve may further comprise the cations at least at a molar equivalent to the conjugated diene in the solution. The cations may be selected from the group consisting of lithium, sodium, potassium, rubidium, and combinations thereof. The cations may be potassium. The solution may comprise the cations at a molar ratio of the cations to the conjugated diene between about 1:1 and 5:1. The solution may have a concentration of the conjugated diene between 0.1 millimolar and 500 millimolar. The solution may have a concentration of the conjugated diene between 0.2 millimolar and 60 millimolar.

The present disclosure is not to be limited in terms of the particular examples or embodiments described in this application, which are intended as illustrations of various aspects. Many modifications and variations can be made without departing from its spirit and scope, as will be apparent to those skilled in the art. Functionally equivalent materials, equipment, methods, and apparatuses within the scope of the disclosure, in addition to those enumerated herein, will be apparent to those skilled in the art from the foregoing descriptions. Such modifications and variations are intended to fall within the scope of the appended claims.

The present disclosure is to be limited only by the terms of the appended claims, along with the full scope of equivalents to which such claims are entitled. It is to be understood that this disclosure is not limited to particular size or shape, methods, reagents, compounds, compositions, or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

All of the patents or publications cited above or herein are hereby incorporated by reference as if set forth in their entirety herein as follows:

Marsili, L.; Bologna, M.; Kojovic, M.; Berardelli, A.; Espay, A. J.; Colosimo, C. Dystonia in Atypical Parkinsonian Disorders. Parkinsonism & Related Disorders 2019, 66, 25-33. https://doi.org/10.1016/j.parkreldis.2019.07.030, Eggers, A. E. Why Do Alzheimer's Disease and Parkinson's Disease Target the Same Neurons? Medical Hypotheses 2009, 72 (6), 698-700. https://doi.org/10.1016/j.mehy.2008.12.047, Changaris, D. Method and Composition for Long Acting Bacterial Suppression on Skin. 9,549,550, Changaris, D. G.; Sullivan, K. I. Methods and Composition for Suppression of Pathogenic Bacterial Growth, Fungal Growth, or Microbial Growth in or on Skin. 10,350,187, 2019, Alonso, R.; Pisa, D.; Marina, A. I.; Morato, E.; Rábano, A.; Carrasco, L. Fungal Infection in Patients with Alzheimer's Disease. J Alzheimers Dis 2014, 41 (1), 301-311. https://doi.org/10.3233/JAD-132681, Alonso, R.; Pisa, D.; Fernández-Fernández, A. M.; Carrasco, L. Infection of Fungi and Bacteria in Brain Tissue From Elderly Persons and Patients With Alzheimer's Disease. Front Aging Neurosci 2018, 10, 159. https://doi.org/10.3389/fnagi.2018.00159, Munoz-Pinto, M. F.; Empadinhas, N.; Cardoso, S. M. The Neuromicrobiology of Parkinson's Disease: A Unifying Theory. Ageing Research Reviews 2021, 70, 101396. https://doi.org/10.1016/j.arr.2021.101396, Niemann, N.; Billnitzer, A.; Jankovic, J. Parkinson's Disease and Skin. Parkinsonism & Related Disorders 2021, 82, 61-76. https://doi.org/10.1016/j.parkreldis.2020.11.017, Pisa, D.; Alonso, R.; Carrasco, L. Parkinson's Disease: A Comprehensive Analysis of Fungi and Bacteria in Brain Tissue. Int J Biol Sci 2020, 16 (7), 1135-1152. https://doi.org/10.7150/ijbs.42257, Petrozziello, T.; Mills, A. N.; Vaine, C. A.; Penney, E. B.; Fernandez-Cerado, C.; Legarda, G. P. A.; Velasco-Andrada, M. S.; Acuña, P. J.; Ang, M. A.; Muñoz, E. L.; Diesta, C. C. E.; Macalintal-Canlas, R.; Acuña-Sunshine, G.; Ozelius, L. J.; Sharma, N.; Bragg, D. C.; Sadri-Vakili, G. Neuroinflammation and Histone H3 Citrullination Are Increased in X-Linked Dystonia Parkinsonism Post-Mortem Prefrontal Cortex. Neurobiology of Disease 2020, 144, 105032. https://doi.org/10.1016/j.nbd.2020.105032, Berstad, K.; Berstad, J. E. R. Parkinson's Disease; the Hibernating Spore Hypothesis. Medical Hypotheses 2017, 104, 48-53. https://doi.org/10.1016/j.mehy.2017.05.022, Anderson, P. N.; Mitchell, J.; Mayor, D. The Uptake of Horseradish Peroxidase by Neuronal Elements within the Guinea-Pig Distal Colon and Its Subsequent Retrograde Transport to the Inferior Mesenteric Ganglion: An in Vitro Study Using an Intact Neuronal System. J Anat 1980, 130 (Pt 1), 153-157, Lagomarsino, V. N.; Kostic, A. D.; Chiu, I. M. Mechanisms of Microbial-Neuronal Interactions in Pain and Nociception. Neurobiology of Pain 2021, 9, 100056. https://doi.org/10.1016/j.ynpai.2020.100056, Beier, K. T. Hitchhiking on the Neuronal Highway: Mechanisms of Transsynaptic Specificity. J Chem Neuroanat 2019, 99, 9-17. https://doi.org/10.1016/j.jchemneu.2019.05.001, Adalsteinsson, J. A.; Kaushik, S.; Muzumdar, S.; Guttman-Yassky, E.; Ungar, J. An Update on the Microbiology, Immunology and Genetics of Seborrheic Dermatitis. Exp Dermatol 2020, 29 (5), 481-489. https://doi.org/10.1111/exd.14091, Food and Drug Administration. GRAS Notice No. GRN 000232 https://wayback.archive-it.org/7993/20170606195602/https://www.fda.gov/Food/Ingredients-PackagingLabeling/GRAS/N oticeInventory/ucm153908.htm, EFSA. Scientific Opinion on the Safety of "Conjugated Linoleic Acid (CLA)-Rich Oil" (Tonalin☐ TG 80) as a Novel Food Ingredient1. EFSA Journal; 2010, 8 (5), 1600, Alonso, Ruth, Diana Pisa, Ana M. Fernández-Fernández, and Luis Carrasco. 2018. "Infection of Fungi and Bacteria in Brain Tissue From Elderly Persons and Patients With Alzheimer's Disease." Frontiers in Aging Neuroscience 10:159. https://doi.org/10.3389/fnagi.2018.00159, Anderson, P. N., J. Mitchell, and D. Mayor. 1980. "The Uptake of Horseradish Peroxidase by Neuronal Elements within the Guinea-Pig Distal Colon and Its Subsequent Retrograde Transport to the Inferior Mesenteric Ganglion: An in Vitro Study Using an Intact Neuronal System." Journal of Anatomy 130 (Pt 1): 153-57, Arsic Arsenijevic, Valentina S, Danica Milobratovic, Aleksandra M Barac, Berislav Vekic, Jelena Marinkovic, and Vladimir S Kostic. 2014. "A Laboratory-Based Study on Patients with Parkinson's Disease and Seborrheic Dermatitis: The Presence and Density of *Malassezia* Yeasts, Their Different Species and Enzymes Production." BMC Dermatology 14 (1): 5. https://doi.org/10.1186/1471-5945-14-5, Bekker, Charissa de. 2019. "*Ophiocordyceps*-Ant Interactions as an Integrative Model to Understand the Molecular Basis of Parasitic Behavioral Manipulation." Current Opinion in Insect Science 33 (June): 19-24. https://doi.org/10.1016/j.cois.2019.01.005, Bentivoglio, M., H. G. J. M. Kuypers, C. E. Catsman-Berrevoets, H. Loewe, and O. Dann. 1980. "Two New Fluorescent Retrograde Neuronal Tracers Which Are Transported over Long Distances." Neuroscience Letters 18 (1): 25-30. https://doi.org/10.1016/0304-3940 (80) 90208-6, Changaris, David G., and Anne L. Carenbauer. 2022. "Potassium Linoleate (Isomerized) Satisfies the United States Environmental Protection Agency MB-05-16 for Hospital Disinfectant on Hard, Non-Porous Surfaces." Cureus 14 (3): e22851. https://doi.org/10.7759/cureus.22851, Changaris, D. G., and K. I. Sullivan. 2019. Methods and composition for suppression of pathogenic bacterial growth, fungal growth, or microbial growth in or on skin. 10,350,187, issued Jul. 16, 2019, Eiser, Arnold R. 2017. "Why Does Finland Have the Highest Dementia Mortality Rate? Environmental Factors May Be Generalizable." Brain Research 1671 (September): 14-17. https://doi.org/10.1016/j.brainres.2017.06.032, Fredericksen, Maridel A., Yizhe Zhang, Missy L. Hazen, Raquel G. Loreto, Colleen A. Mangold, Danny Z. Chen, and David P. Hughes. 2017. "Three-Dimensional Visualization and a Deep-Learning Model Reveal Complex Fungal Parasite Networks in Behaviorally Manipulated Ants." Proceedings of the National Academy of Sciences 114 (47): 12590-95. https://doi.org/10.1073/pnas. 1711673114, Fukasawa, Yu, Melanie Savoury, and Lynne Boddy. 2020. "Ecological Memory and Relocation Decisions in Fungal Mycelial Networks: Responses to Quantity and Location of New Resources." The ISME Journal 14 (2): 380-88. https://doi.org/10.1038/s41396-019-0536-3, Hywel-Jones, Nigel L. 1996. "*Cordyceps* Myrmecophila-like Fungi Infecting Ants in the Leaf Litter of Tropical Forest in Thailand." Mycological Research 100 (5): 613-19. https://doi.org/10.1016/S0953-7562 (96) 80017-7, Kashem, Sakeen W., and Daniel H. Kaplan. 2016. "Skin Immunity to *Candida Albicans*." Trends in Immunology 37 (7): 440-50. https://doi.org/10.1016/j.it.2016.04.007, Libersat, Frederic, Maayan Kaiser, and Stav Emanuel. 2018. "Mind Control: How Parasites Manipulate Cognitive Functions in Their Insect Hosts." Frontiers in Psychology 9 (May): 572. https://doi.org/10.3389/fpsyg.2018.00572, Lovett, Brian, Raymond J. St. Leger, and Henrik H. de Fine Licht. 2020. "Going Gentle into That Pathogen-Induced Goodnight." Journal of Invertebrate Pathology 174 (July): 107398. https://doi.org/10.1016/j.jip.2020.107398, Munoz-Pinto, Mario F., Nuno Empadinhas, and Sandra M. Cardoso. 2021. "The Neuromicrobiology of Parkinson's Disease: A Unifying Theory." Ageing Research Reviews 70 (September): 101396. https://doi.org/10.1016/j.arr.2021.101396, Piccinotti, Silvia, and Sean P. J. Whelan. 2016. "Rabies Internalizes into Primary Peripheral Neurons via Clathrin Coated Pits and Requires Fusion at the Cell Body." Edited by Mark T. Heise. PLOS Pathogens 12 (7): e1005753. https://doi.org/10.1371/journal.ppat.1005753, Diana, Ruth Alonso, and Luis Carrasco. 2020. "Parkinson's Disease: A Comprehensive Analysis of Fungi and Bacteria in Brain Tissue." International Journal of Biological Sciences 16 (7): 1135-52. https://doi.org/10.7150/ijbs.42257, Pisa, Diana, Ruth Alonso, Angeles Juarranz, Alberto Rábano, and Luis Carrasco. 2015. "Direct Visualization of Fungal Infection in Brains from Patients with Alzheimer's Disease." Journal of Alzheimer's Disease: JAD 43 (2): 613-24. https://doi.org/10.3233/JAD-141386, Prior, Robert, Lawrence Van Helleputte, Veronick Benoy, and Ludo Van Den Bosch. 2017. "Defective Axonal Transport: A Common Pathological Mechanism in Inherited and Acquired Peripheral Neuropathies." Neurobiology of Disease 105 (September): 300-320. https://doi.org/10.1016/j.nbd.2017.02.009, Ravn Jørgensen, Astrid-Helene, Jacob P Thyssen, and Alexander Egeberg. 2017. "Skin Disorders in Parkinson’s Disease: Potential Biomarkers and Risk Factors." Clinical, Cosmetic and Investigational Dermatology Volume 10 (March): 87-92. https://doi.org/10.2147/CCID.S130319, Schneider, Marlon R., Ruth Schmidt-Ullrich, and Ralf Paus. 2009. "The Hair Follicle as a Dynamic Miniorgan." Current Biology 19 (3): R132-42. https://doi.org/10.1016/j.cub.2008.12.005, Tang, H. Z., A. Tsai, and R. Hammerschlag. 1994. "Selective Inhibition of Neuronal Protein Synthesis by Retrogradely Transported Ricin." Journal of Neuroscience Methods 55 (1): 15-22. https://doi.org/10.1016/0165-0270 (94) 90035-3, Vigasova, Dana, Michal Nemergut, Barbora Liskova, and Jiri Damborsky. 2021. "Multi-Pathogen Infections and Alzheimer's Disease." Microbial Cell Factories 20 (1): 25. https://doi.org/10.1186/s12934-021-01520-7, Xu, Xiangmin, Todd C. Holmes, Min-Hua Luo, Kevin T. Beier, Gregory D. Horwitz, Fei Zhao, Wenbo Zeng, May Hui, Bert L. Semler, and Rozanne M. Sandri-Goldin. 2020. "Viral Vectors for Neural Circuit Mapping and Recent Advances in Trans-Synaptic Anterograde Tracers." Neuron 107 (6): 1029-47. https://doi.org/10.1016/j.neuron.2020.07.010.

The patents and publications listed above are herein incorporated by reference as if set forth in their entirety. The purpose of incorporating the patents and publications is solely to provide additional information relating to technical features of one or more embodiments, which information may not be completely disclosed in the wording in the pages of this application. Words relating to the opinions and judgments of the author and not directly relating to the technical details of the description of the embodiments therein are not incorporated by reference. The words all, always, absolutely, consistently, preferably, guarantee, particularly, constantly, ensure, necessarily, immediately, endlessly, avoid, exactly, continually, expediently, need, must, only, perpetual, precise, perfect, require, requisite, simultaneous, total, unavoidable, and unnecessary, or words substantially equivalent to the above-mentioned words in this sentence, when not used to describe technical features of one or more embodiments, are not considered to be incorporated by reference herein.

The invention claimed is:

1. A method of reducing the symptoms of neurodegenerative disease in a human comprising:
    applying to the human a solution or a salve to at least one of the skin, the mouth, the nasal cavities, the lungs, the eyes, or the vagina of the human;
    wherein the applied solution or the applied salve comprises an effective amount of an isomerized or conjugated linoleic acid cation salt having a conjugated diene for at least a measurable improvement in the movement or mental acuity of the human;
    wherein the conjugated diene has a structure of —C=C—C=C—;
    wherein the salt comprises cations and anions, the cations are at a molar ratio of the cations to the conjugated diene between about 1.5:1 and 4.5:1; and
    wherein the measurable improvement in the movement or mental acuity of the human is within 4-6 weeks of the applying of the solution or the salve.

2. The method of claim 1, wherein the applying of the solution or the salve comprises applying the salve to the human.

3. The method of claim 1, wherein the applying the conjugated diene consists essentially of applying substantially pure cis-9, trans-11 conjugated linoleic acid.

4. The method of claim 1, wherein the neurodegenerative disease is one of Dystonia, Parkinson's, Alzheimer's, and Amyotrophic Lateral Sclerosis.

5. The method of claim 1, wherein the solution or the salve comprises at least one of water, amino acid, and alcohol.

6. The method of claim 1, wherein the cations are selected from the group consisting of lithium, sodium, potassium, rubidium, and combinations thereof.

7. The method of claim 6, wherein the cations comprise potassium.

8. The method of claim 1, wherein the cations are at a molar ratio of the cations to the conjugated diene between about 2.5:1 and 3.5:1.

9. The method of claim 1, wherein the solution or the salve comprises a concentration of the conjugated diene between about 0.1 millimolar and about 500 millimolar.

10. The method of claim 9, wherein the solution or the salve comprises a concentration of the conjugated diene between about 0.2 millimolar and about 60 millimolar.

11. The method of claim 1, further comprising an initial measuring of a rotation of a wrist of the human, prior to the applying the solution or the salve, and a subsequent measuring of the rotation of the wrist of the human, after the applying the solution or the salve, wherein the measuring of the rotation of the wrist comprises grasping a handle, rotating the wrist and thereby moving a push tool, the push tool moves a first marker and a second marker, the location of the moved first marker measures the maximum rotation of the wrist in a first direction and the location of the moved second marker measures the maximum rotation of the wrist in a second direction.

12. The method of claim 11, wherein the measuring of the rotation of the rotation of the wrist is performed with a wrist rotation measuring device comprising:
    a forearm support;
    a strap configured and disposed to hold a forearm on the forearm support;
    the handle;
    a rod extending from the handle;
    an actuator in communication with the rod;
    the push tool disposed in communication with the actuator; and
    wherein the push tool is configured and disposed to move the first and the second marker upon the rotating of the wrist in the first direction and in the second direction.

13. The method of claim 1, wherein the isomerized or conjugated linoleic acid cation salt comprises safflower oil saponified with potassium hydroxide at a weight ratio of about 3 gm potassium hydroxide to 7 gm safflower, or about 3:7.

14. The method of claim 1, wherein the cations are at a molar ratio of the cations to the conjugated diene of about 3:1.

* * * * *